(12) United States Patent
Xiang et al.

(10) Patent No.: US 10,035,750 B2
(45) Date of Patent: Jul. 31, 2018

(54) PREPARATION METHOD FOR POLYUNSATURATED FATTY ACID-CALCIUM

(71) Applicant: Zhejiang Medicine Co., Ltd. Xinchang Pharmaceutical Factory, Zhejiang Province (CN)

(72) Inventors: Xuebing Xiang, Zhejiang Province (CN); Xinde Xu, Zhejiang Province (CN); Bin Shao, Zhejiang Province (CN); Yufang Meng, Zhejiang Province (CN); Chong Li, Zhejiang Province (CN)

(73) Assignee: ZHEJIANG MEDICINE CO., LTD. XINCHANG PHARMACEUTICAL FACTORY, Xinchang County, Zhejiang Province (CN)

( * ) Notice: Subject to any disclaimer, the term of this patent is extended or adjusted under 35 U.S.C. 154(b) by 0 days.

(21) Appl. No.: 15/519,086

(22) PCT Filed: Oct. 12, 2015

(86) PCT No.: PCT/CN2015/000686
§ 371 (c)(1),
(2) Date: Apr. 13, 2017

(87) PCT Pub. No.: WO2016/058283
PCT Pub. Date: Apr. 21, 2016

(65) Prior Publication Data
US 2017/0226445 A1     Aug. 10, 2017

(30) Foreign Application Priority Data
Oct. 13, 2014 (CN) .......................... 2014 1 0538583

(51) Int. Cl.
*C07C 51/41* (2006.01)
*C11C 1/02* (2006.01)
*C11C 3/12* (2006.01)
*A23K 20/158* (2016.01)

(52) U.S. Cl.
CPC .......... *C07C 51/412* (2013.01); *A23K 20/158* (2016.05); *C11C 1/025* (2013.01); *C11C 3/126* (2013.01)

(58) Field of Classification Search
CPC ....... C07C 51/412; C07C 51/41; C07C 57/03; C07C 57/12
See application file for complete search history.

(56) References Cited

U.S. PATENT DOCUMENTS

| 4,235,794 | A   | * | 11/1980 | Rieber .................. C07C 51/412 106/471 |
| 5,382,678 | A   |   | 1/1995  | Vinci et al. |
| 6,392,075 | B1  | * | 5/2002  | Strohmaier ........... C07C 51/412 426/807 |
| 8,178,707 | B2  | * | 5/2012  | Gleason ................ C07C 51/412 554/156 |
| 8,203,013 | B2  | * | 6/2012  | Hsu ........................ C07C 51/41 554/156 |
| 2002/0137958 | A1 |  | 9/2002  | Strohmaier et al. |
| 2009/0182050 | A1 |  | 7/2009  | Barrow et al. |

FOREIGN PATENT DOCUMENTS

| CN | 1270160  | 10/2000 |
| CN | 1562944  | 1/2005  |
| CN | 1685921  | 10/2005 |
| CN | 1752064  | 3/2006  |
| CN | 102417444 | 4/2012 |
| WO | 9429256  | 12/1994 |

OTHER PUBLICATIONS

International Search Report issued for PCT/CN2015/000686 dated Feb. 6, 2016. English translation, 4 pages.

* cited by examiner

*Primary Examiner* — Yate' K Cutliff
(74) *Attorney, Agent, or Firm* — Hamre, Schumann, Mueller & Larson, P.C.

(57) ABSTRACT

The present invention relates to a preparation method for a polyunsaturated fatty acid-calcium, primarily comprising directly reacting a polyunsaturated fatty acid material with a water-soluble calcium compound to obtain a polyunsaturated fatty acid-calcium salt. The present invention has a simple technical process, short reaction time, and high reaction yield. The produced polyunsaturated fatty acid-calcium product is of high quality, and relatively less byproducts and waste water are produced. The process is overall environmentally friendly and has small safety risks, and is suitable for scaled production.

11 Claims, No Drawings

PREPARATION METHOD FOR POLYUNSATURATED FATTY ACID-CALCIUM

FIELD OF THE INVENTION

The present invention relates to a preparation method for a polyunsaturated fatty acid-calcium, especially relates to a preparation of a polyunsaturated fatty acid-calcium in various forms of polyunsaturated fatty acid materials, primarily comprising directly reacting a polyunsaturated fatty acid material with a water-soluble calcium compound to obtain a polyunsaturated fatty acid-calcium salt. The method of the present invention is simple, and has lower reaction temperature and less destruction to the polyunsaturated fatty acid-calcium material. And the method greatly promotes a calcification degree by water-soluble calcium compounds, shortens reaction time, improves reaction yield. The final polyunsaturated fatty acid product is of high quality.

BACKGROUND OF THE INVENTION

As people pay more and more attention to their health and healthy diet, many related products have been widely recognized and accepted. Wherein polyunsaturated fatty acid products play an important role in market. Raw materials as pharmaceuticals or dietary supplements or feed additives have a broader development and application prospect.

PUFA is a component of cell membrane. PUFA is an important basic substance for body metabolism, especially for infant brain development. PUFA mainly plays a role on physiological functions such as maintaining cell membrane fluidity, promoting cholesterol esterfication, reducing cholesterol and triglycerides levels, decreasing blood viscosity, and improving blood circulation and so on. Furthermore, PUFA can also have functions such as improving human thinking and enhancing memory. Lacking PUFA would result in many connate or acquired diseases. However, PUFA cannot be synthesized by the body itself. PUFA must be obtained from diet.

There are various kinds of PUFA including ω-3 PUFA, ω-6 PUFA, ω-9 PUFA, and other kinds of conjugated linoleic acid, such as α-Linolenic acid (ALA), eicosapentaenoic ester (EPA), docosahexaenoic acid (DHA), docosapentaenoic acid (DPA), linoleic acid (LA), conjugated linoleic acid (CLA), γ-linolenic acid (GLA), arachidonic acid (AA) and so on. Wherein EPA and DHA representing ω-3 PUFA are known and acceptable to the public and obviously improve human thinking and enhance memory. Their molecular structures of polyunsaturated fatty acids are as follows.

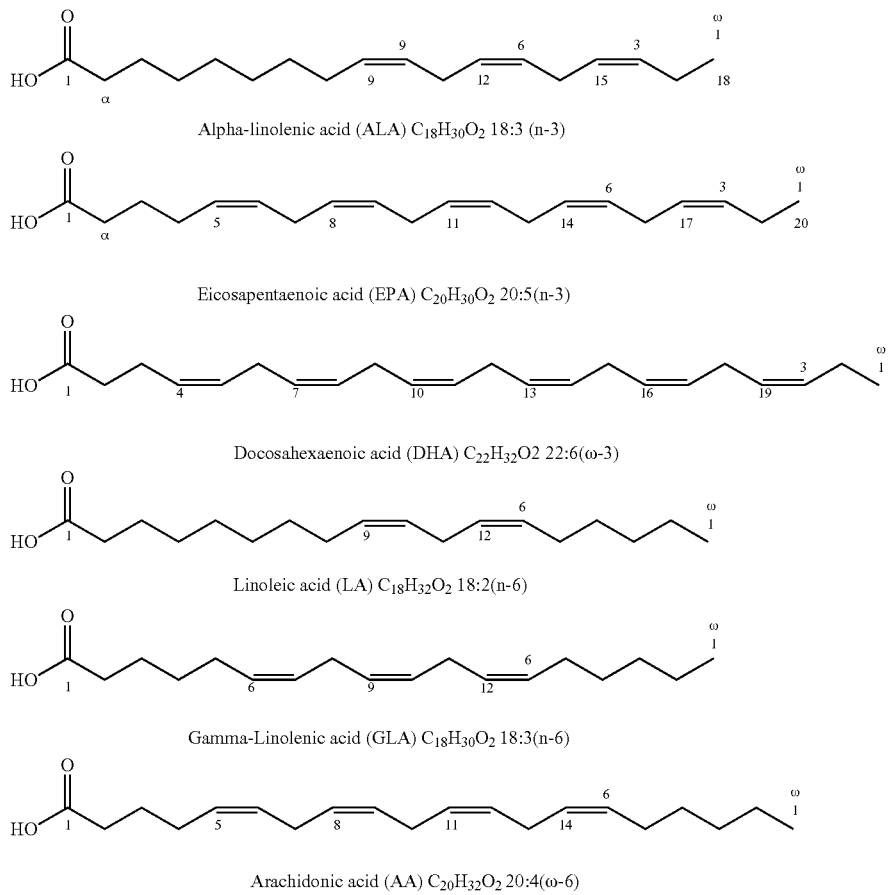

Alpha-linolenic acid (ALA) $C_{18}H_{30}O_2$ 18:3 (n-3)

Eicosapentaenoic acid (EPA) $C_{20}H_{30}O_2$ 20:5(n-3)

Docosahexaenoic acid (DHA) $C_{22}H_{32}O_2$ 22:6(ω-3)

Linoleic acid (LA) $C_{18}H_{32}O_2$ 18:2(n-6)

Gamma-Linolenic acid (GLA) $C_{18}H_{30}O_2$ 18:3(n-6)

Arachidonic acid (AA) $C_{20}H_{32}O_2$ 20:4(ω-6)

Polyunsaturated fatty acids mainly derive from algae extract and marine oil, one of important sources comes from fish oil.

Liquid raw materials of polyunsaturated fatty acid product absorbed by the body mainly includes free-type polyunsaturated fatty acids, ethyl ester-type polyunsaturated fatty acids, glyceride-type polyunsaturated fatty acids. These raw materials have related functions and also have a series of deficiencies. First of all, these products exist in liquid form and have certain fishy smell. It would make some people have certain psychological resistance and consequently would not be accepted by the public. So it have some limitation in scope of uses. Secondly, absorption and utilization of some products are also not sufficient in the body, and then the bioavailability of some products is lower and so on.

Polyunsaturated fatty acid-calcium products can make up for the above deficiencies to a certain extent. First of all, polyunsaturated fatty acid-calcium products as a quality source of calcium can supplement calcium nutrition needed for the body. Besides it does not undermine effects on polyunsaturated fatty acids. Secondly, polyunsaturated fatty acid-calcium products exist in the form of free-flowing powder product, and consequently have broader application scope of polyunsaturated fatty acids. The products have no peculiar smell, good stability, and other advantages. The products can improve the bioavailability of polyunsaturated fatty acids for the body to some extent.

At present, processes of preparing polyunsaturated fatty acid-calcium products mainly include directly melting glyceride-type polyunsaturated fatty acids with calcium oxide or calcium hydroxide to obtain polyunsaturated fatty acid-calcium; or melting free-type polyunsaturated fatty acids with calcium oxide or calcium hydroxide to obtain polyunsaturated fatty acid-calcium; or firstly various of ester-type polyunsaturated fatty acids are saponified to obtain polyunsaturated fatty acid sodiums, and then perform an ion exchange of sodium and calcium to obtain polyunsaturated fatty acid-calcium products. But the above processes have some deficiencies.

One of processes is to directly perform a calcification of raw materials of calcium oxide or calcium hydroxide in a molten state with glyceride-type polyunsaturated fatty acids or free-type polyunsaturated fatty acids to obtain polyunsaturated fatty acid-calcium products. Firstly, polyunsaturated fatty acids are easy to cause oxidation, decomposition or polymerization and other destructive effects at the temperature because the reaction temperature is higher up to more than 200~300° C. Secondly, calcium oxides or calcium hydroxides do not dissolve in a reaction system because of poor solubility. It could result in lower reaction degree, longer reaction time, lower reaction yield and other shortcomings, and then finally polyunsaturated fatty acid-calcium products have poorer quality.

Another process is to firstly perform a saponification of methyl ester-type, ethyl ester-type or glyceride-type polyunsaturated fatty acids with liquid alkali to obtain polyunsaturated fatty acid-sodium, or then acidify to obtain polyunsaturated fatty acids; and afterwards react polyunsaturated fatty acid sodium or free-type polyunsaturated fatty acid with various of calcium compounds to obtain polyunsaturated fatty acid-calcium, wherein the calcium compounds include calcium oxide, calcium hydroxide, calcium acetate, calcium lactate, calcium chloride. But the process is more complicated. Wherein the first step is to perform a saponification, a large number of polyunsaturated fatty acids are destroyed under a strong alkaline condition due to addition of a large amount of liquid alkali. It could make color of intermediate and final products darker and make product quality lower. Secondly, it could decrease reaction degree and reduce product yield because calcium oxide and calcium hydroxide are almost insoluble in water or various of organic solvents or various of polyunsaturated fatty acids in a reaction system. Besides, the process is more complicated because the process overall includes saponification, pickling, washing, recovery of solvents, calcification, filtration, drying, grinding and other processes. And the quality of final products is poor, and has lower yield and the process could produce a large amount of wastewater.

There have been a series of methods of preparing for polyunsaturated fatty acid-calcium products.

U.S. Pat. No. 5,382,678 directly performs a calcification of glyceride-type fish oil polyunsaturated fatty acid with calcium oxide or calcium hydroxide at 250° C. The process is not sufficient and lower yield, although selecting glyceride-type polyunsaturated fatty acids with higher boiling point and slightly better oxidation resistance could overcome impact of high temperature on raw materials to a certain extent, the content of glyceride-type fish oil in the final product is merely more than 10%, and the product is too stickiness to form a free-flowing powder product.

Patents U.S. 60/724,644, U.S. 60/775,664 describe a process of direct performing a calcification of calcium oxide or calcium hydroxide with free-type polyunsaturated fatty acids or various esters-type of polyunsaturated fatty acids. But the process has higher reaction temperature, lower reaction degree and poor product quality. Another process is to perform a saponification of various of ester-type polyunsaturated fatty acids to obtain polyunsaturated acid sodium firstly, and then to perform ion exchange to obtain a polyunsaturated acid-calcium. But the process has longer route, produces more wastewater and lower yield.

U.S. patent Ser. No. 09/675,745 relates to a process of heating polyunsaturated fatty acid firstly, then adding a hydrate of calcium oxide slowly, finally evaporating water and other procedures. But the process is carried out in a special environment, and has complicated, lower reaction degree, poor product quality, because calcium oxide is insoluble in water.

Patent CN1270160 describes a process of preparing free-type fatty acid by saponification and acidification in turn, and then reacting purified free-type fatty acid with calcium hydroxide to obtain polyunsaturated fatty acid-calcium products. But the process has longer reaction time, lower reaction degree, lower yield, because calcium oxide is insoluble in water.

Patent CN102417444 describes a process of directly reacting fatty acids with calcium hydroxide or calcium oxide to obtain fatty acid-calcium. Wherein the process uses a continuous mode to improve reaction yield by continuous precipitation of fatty acid-calcium mode, and finally obtains 80~85% of yield. But the process produces a large amount of wastewater, and has lower product purity.

Patents CN1752064, CN1685921 describes a process of performing a saponification of fatty acids with liquid alkal to obtain fatty acid sodium, and then performing an ion exchange with calcium chloride to obtain fatty acid-calcium products. But the process route is complicated, and has 80% lower yield and produces a large number of chlorine-containing wastewater, and then results in a serious pollution to environment.

On the whole, most of preparation methods of polyunsaturated fatty acid-calcium products in the prior art mainly have at least one of the following problems: 1) insoluble calcium oxide or calcium hydroxide resulting in lower reaction degree, longer reaction time, lower yield and other problems because of using calcium oxide or calcium hydroxide as raw materials; 2) uses of high temperature condition or liquid alkali resulting in a large amount of polyunsaturated fatty acid damaged and poor product quality.

Generally speaking, main materials of preparing for polyunsaturated fatty acid-calcium products are polyunsaturated fatty acids and calcium compounds. But polyunsaturated fatty acids including free-type polyunsaturated fatty acids and esters-type polyunsaturated fatty acids are not stable because these compounds contain more double bond groups. Wherein free-type polyunsaturated fatty acids have a lower boiling point and the least oxidation resistance; methyl ester-type or ethyl ester-type polyunsaturated fatty acids take second place; and glyceride-type polyunsaturated fatty acids with the highest boiling point are relatively stable. But glyceride-type polyunsaturated fatty acid is prone to polymerization to form polymers at more than 260° C. Besides, polyunsaturated fatty acids are prone to produce structure damaged and curing matter state with darker color appearance because polyunsaturated fatty acids are more sensitive to strong acid or strong alkali environment.

There are some limitation for selection of calcium compounds. Calcium oxide or calcium hydroxide is a common use. Compounds having a certain basicity are easy to react with polyunsaturated fatty acids in theory. However, polyunsaturated fatty acids and calcium cannot fully contact together because of heterogeneous reaction of liquid and solid, and produce low reaction degree because of insolubility of calcium oxide or calcium hydroxide itself. Even polyunsaturated fatty acid-calcium product encases calcium compounds and thereby inhibit continuation reaction because of production of insoluble polyunsaturated fatty acid-calcium product. Eventually it would lead to a long reaction time, lower content of product.

In addition, water-soluble calcium compound is relatively little, the main reason is to obtain polyunsaturated fatty acid sodium by saponification of polyunsaturated fatty acid by using a large number of liquid alkali and water in the process. So it would make polyunsaturated fatty acid material destroyed, decrease product quality and produce a large amount of wastewater.

SUMMARY OF THE INVENTION

In order to overcome the above deficiencies, the present invention creatively uses an aqueous solution of water-soluble calcium compound material directly reacting with a polyunsaturated fatty acid to obtain a polyunsaturated fatty acid-calcium. The polyunsaturated fatty acid-calcium is continuously precipitated during the reaction because of insolubility of polyunsaturated fatty acid-calcium in reaction system. So the reaction can be conducted well with higher reaction degree. And the process has also better reactivity and higher reaction degree by using polyunsaturated fatty acid materials comprising free-type polyunsaturated fatty acid or ester-type polyunsaturated fatty acids The present invention relates to a method of preparing a polyunsaturated fatty acid-calcium, especially relates to various forms of polyunsaturated fatty acid fish oil materials used for preparing the polyunsaturated fatty acid product.

The method of preparing a polyunsaturated fatty acid-calcium of the present invention comprises the following steps:

1) dissolving calcium compound materials: dissolving an appropriate molar equivalent of a water-soluble calcium compound material in a certain amount of water, to obtain an aqueous solution of calcium compound;

2) feeding: feeding a polyunsaturated fatty acid to the aqueous solution of calcium compound in a certain reaction condition under stirring for a time; and 3) processing product: filtering the reaction solution to obtain a solid of polyunsaturated fatty acid-calcium after completion of the reaction, and then drying and crushing the solid of polyunsaturated fatty acid-calcium, to obtain a free-flowing polyunsaturated fatty acid-calcium product.

It may be known by relevant quality test that the product has good quality and has a higher yield.

The term "a certain reaction condition" described in the present invention is relatively mild, which is referred to as at −20~100° C. of the reaction temperature, preferably 20~100° C. And the reaction time is 0.5~10 hours, preferably 0.5~3 hours.

In the present invention, the molar weight of the fatty acid in the polyunsaturated fatty acid material and polyunsaturated fatty acid-calcium product is determined by a common test method. In particular, a sample to be tested is completely saponified and then acidified to obtain a completely free-type polyunsaturated fatty acid sample, and then titrate acid value of the sample, and calculate an average molar mass of the sample according to the acid value, thereby obtain a molar weight of the sample.

Test step: 1.0 g of the sample is added to a wild-mouth bottle, 20 ml of ethyl alcohol and 2~3 drops of phenolphthalein indicator are added to the wild-mouth bottle and shaked up, and then titrate with 0.1 mol/L of potassium hydroxide standard solution (C mol/L), wherein V ml of the potassium hydroxide standard solution is consumed, and the acid value of the sample is (56*C*V)/W (unit is mgKOH/g), an average molar mass of the sample is (1000*W)/(C*V), and the molar weight of fatty acid in the final sample is a ratio of a mass to a mean molar mass.

A process of treating wastewater and byproducts of the present invention includes the following steps: filtering the reaction solution mainly containing water, trace organic acids and alcohol substances, etc., and then separating organics by atmospheric distillation or vacuum distillation. So organics can be recycled, wastewater discharged can reach a discharge standard for direct discharging. The wastewater discharged will not produce pollution and will not harm to environment.

Due to have good dissolution and reactivity of the process, the scope of polyunsaturated fatty acid material of the present invention is widely obtained, basically comprising various forms of polyunsaturated fatty acids or mixtures thereof, such as free-type polyunsaturated fatty acids, methyl ester-type polyunsaturated fatty acids, ethyl ester-type polyunsaturated fatty acids, glyceride-type polyunsaturated fatty acids, specifically comprising a polyunsaturated fatty acid with a formula

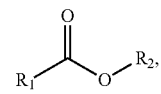

wherein $R_1$ is a $C_6$~$C_{40}$ alkenyl group, $R_2$ is H or a $C_1$~$C_4$ alkyl group; and a polyunsaturated fatty acid with a formula

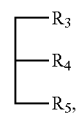

wherein $R_3$, $R_4$, $R_5$ are a hydroxyl or a $C_1$~$C_4$ carboxylic acid group or a $C_6$~$C_{40}$ carboxylic acid group containing one or more double bonds; $R_3$, $R_4$ and $R_5$ can be the same or different; and $R_3$, $R_4$ and $R_5$ cannot be simultaneously a hydroxyl group or a $C_1$~$C_4$ carboxylic acid group;

The term "polyunsaturated fatty acid material" described in the present invention is referred to as one or more polyunsaturated fatty acids with various content of fish oil (ω-3 polyunsaturated fatty acid extracted directly), algae oil (ω-3 polyunsaturated fatty acid from fermentation), linoleic acid, conjugated linoleic acid, linolenic acid, arachidonic acid, wherein the total content of the polyunsaturated fatty acid is 10~100 wt %.

Moreover, no limitation is basically for sources of polyunsaturated fatty acids. Polyunsaturated fatty acid materials including algae extract and aquatic animal oil (such as fish oil) have a good reaction activity, wherein 10~100 wt % of the polyunsaturated fatty acid content in the polyunsaturated fatty acid material does not have a greater influence on the process and reaction yield, and the polyunsaturated fatty acid-calcium products obtained by the process have basically higher yield and better quality.

The calcium compound of the present invention is water-soluble calcium compounds. Feeding mode adopts a form of an aqueous solution of water-soluble calcium compounds. Consequently it can greatly promote the calcification degree of the present process, improve the quality of the polyunsaturated fatty acid-calcium product. The process achieves purposes of high efficiency of the process, energy conservation, safety and environment protection by reducing process conditions, wherein the "water-soluble calcium compound material" is selected from the group consisting of calcium acetate, calcium lactate, calcium chloride, calcium nitrate, calcium citrate, and calcium fumarate.

Feeding ratio of the process is as follows: the molar equivalent of the water-soluble calcium compound material is 0.1~0.9 relative to a molar weight of polyunsaturated fatty acid, preferably 0.5~0.7. Wherein the water amount of dissolving the water-soluble calcium compound is 1~40 times as much as the weight of the water-soluble calcium compound. When the polyunsaturated fatty acid material and the water-soluble calcium compound material are excess in accordance with the reaction equivalent weight or the water-soluble calcium compound material, the yield of the calcification is higher, and the excessive calcium dissolved in water will not affect on product quality. And when the polyunsaturated fatty acid material is excess, the excessive amount of polyunsaturated fatty acid can indirectly achieve purposes of increasing the yield and reducing the loss through late recovery and application. In addition, the water amount for dissolving the water-soluble calcium compound mainly depends on solubility of the calcium compound in water, basically is a water amount or excess water for the complete dissolution of the calcium compound, wherein excess water has little effect on the process.

The present invention creatively utilizes a water-soluble calcium compound directly reacting with a polyunsaturated fatty acid material to obtain polyunsaturated fatty acid-calcium salts. The process is very simple. The main steps include dissolving calcium compound, calcification, filtration, drying and crushing. The process has lower reaction temperature, less destruction to polyunsaturated fatty acid materials, and the water-soluble calcium compound greatly promotes calcification degree, shortens reaction time and improves reaction yield, and has better quality of polyunsaturated fatty acid products finally.

Adopting an aqueous solution of calcium compound makes the aqueous solution of calcium compound fully contact and react with a polyunsaturated fatty acid materials in the process of the present invention. So it could greatly promote calcification degree, shorten reaction time and increases reaction yield and avoids uses of strong bases or strong acids. Besides the reaction temperature is lower and the reaction condition is mild. So the polyunsaturated fatty acid material are not damaged, and the product quality is better finally.

Furthermore, wastewater and the byproducts produced by the process, are less. Wastewater is mainly derived from water of dissolving calcium compounds, Byproducts are organic acids, alcohols and other substances. After completion of the reaction, a filtrate is obtained by filtration and separated into byproducts by simple recovery. Byproducts can be utilized, and wastewater can be discharged directly, which can achieve a direct discharge standard, and will not cause pollution to environment.

In compared with other prior processes, the process of the present invention has relatively simple and easy to operate, and has better reaction activity, shorten reaction time, increase reaction degree, and has mild reaction condition, better product quality, higher yield and better process stability. The process is generally better in safety and environment protection and is very suitable for large-scale industrial production.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

To add 0.5 mol of calcium acetate (79.9 g) into 200 g of water for dissolution completely to obtain an aqueous solution of calcium acetate. To add 1.0 mol of a free-type fish oil material (EPA34.7%, DHA 23.6%, and the total content of the free-type polyunsaturated fatty acid is 63.2%) into a reaction flask under stirring, and then heat to 40° C. Afterwards, to add the aqueous solution of calcium compound into the reaction flask, and then stir for 2.0 hours. To filter a solution after completion of the reaction, to obtain a filtered cake solid. The filtered cake solid is then dried, crushed to obtain a free-flowing fish oil polyunsaturated fatty acid-calcium product.

A filtrate by filtration is subjected to a simple distillation or vacuum distillation to obtain a small amount of available organics and wastewater. The wastewater can reach a discharge standard for directly discharge.

It may be seen by testing the polyunsaturated fatty acid-calcium fish oil product that the molar quantity of the polyunsaturated fatty acid-calcium fish oil product is 0.95 mol, the total content of polyunsaturated fatty acid-calcium is 62.9%, wherein the content of EPA is 33.9%, the content of DHA is 23.2%, the total free-type polyunsaturated fatty acid is 0.1%, the product yield is 94.5%, the product color is white, and the product quality is better.

Comparative Example 2

To add 1.0 mol of a free-type fish oil material (EPA34.7%, DHA 23.6% and the total content of the free-type polyunsaturated fatty acid 63.2%) and 0.5 mol of calcium oxide into a reaction flask under stirring, and then heat to 250° C. for 2.0 hour, to obtain a solid by cooling after completion of the reaction, and then dry and crush to obtain a fish oil polyunsaturated fatty acid-calcium product, the viscosity of the product is larger, the product color is darker.

It may be seen by testing polyunsaturated fatty acid-calcium fish oil product that the molar quantity of the polyunsaturated fatty acid-calcium fish oil product is 0.63 mol, the total content of the polyunsaturated fatty acid-calcium is 10.7%, wherein the content of EPA is 11.2%, the content of DHA is 6.1%, the total free-type polyunsaturated fatty acid is 12.3%, the product yield is 10.7%, and the product quality is poorer.

It can be seen from Example 1 of the present invention that the process obtains an aqueous solution of calcium acetate by dissolving a water-soluble calcium acetate material in water, and the aqueous solution is reacted with a free-type fish oil material at lower temperature by a mild condition to obtain a polyunsaturated fatty acid-calcium fish oil product. The process is overall simple and easy to operate, has very high reaction degree, higher yield and better product quality.

The comparative example 2 selects 250° C. as a temperature condition to obtain a polyunsaturated fatty acid-calcium fish oil product by conventional reaction of calcium oxide material. But the reaction cannot be carried out at a low temperature condition. The reaction degree is lower, because the solubility of calcium oxide is very poor. Besides the content of the polyunsaturated fatty acid-calcium fish oil product is obviously low because a larger part of the raw material or product is seriously destroyed at high temperature. So the product yield is very low, and the product quality is poor.

Examples 3~10

The objects of related parameters of Examples 3~10 are listed in the following Table.

It can be seen from Examples 3~15 of the present invention that the process obtains an aqueous solution of calcium acetate by dissolving a water-soluble calcium acetate material in water, and the aqueous solution is reacted with a free-type fish oil material at low temperature and a mild condition to obtain a polyunsaturated fatty acid-calcium fish oil product. The process is overall simple and easy to operate, has very high reaction degree, and the product yield is higher than 93.4%, and the product quality is better.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. A method of preparing a polyunsaturated fatty acid-calcium, comprising the following step:
   (i) dissolving a water-soluble calcium compound material or a mixture of several water-soluble calcium compound materials in an appropriate amount of water to obtain an aqueous solution of calcium compound;
   (ii) adding the aqueous solution of calcium compound to a polyunsaturated fatty acid material for a reaction at a reaction temperature of −20~100° C., wherein the

| Example | Polyunsaturated fatty acid material | Total content of polyunsaturated fatty acid (%) | Calcium compound (mol/mol) | Water (g/g) | Temperature (° C.) | Reaction time (Hr) | Total content of polyunsaturated fatty acid-calcium (%) | Yield (%) |
|---|---|---|---|---|---|---|---|---|
| 3 | Methyl ester-type fish oil | 98.3 | Calcium acetate 0.5 | 5 | 20° C. | 3 | 97.9 | 96.6 |
| 4 | Ethyl ester-type fish oil | 68.8 | Calcium acetate 0.6 | 6 | 40° C. | 3 | 68.2 | 95.5 |
| 5 | Glyceride-type fish oil | 47.2 | Calcium chloride 0.5 | 2 | 30° C. | 0.5 | 46.3 | 94.8 |
| 6 | Free-type algae oil | 68.5 | Calcium lactate 0.7 | 20 | 50° C. | 3 | 68.0 | 95.2 |
| 7 | Ethyl ester-type algae oil | 53.6 | Calcium nitrate 0.6 | 1 | 100° C. | 2 | 53.1 | 96.0 |
| 8 | Free-type linoleic acid | 92.7 | Calcium citrate 0.5 | 30 | 30° C. | 1 | 92.0 | 93.9 |
| 9 | Glyceride-type linoleic acid | 46.9 | Calcium lactate 0.9 | 40 | 50° C. | 3 | 46.2 | 94.8 |
| 10 | Free-type conjugated linoleic acid | 13.9 | Calcium chloride 0.5 | 4 | 30° C. | 10 | 13.3 | 96.0 |
| 11 | Ethyl ester-type conjugated linoleic acid | 27.7 | Calcium fumarate 0.7 | 8 | 40° C. | 3 | 26.8 | 96.2 |
| 12 | Free-type linolenic acid | 53.8 | Calcium citrate 0.6 | 7 | 80° C. | 8 | 52.8 | 94.8 |
| 13 | Ethyl ester-type linolenic acid | 42.6 | Calcium acetate 0.5 | 9 | 30° C. | 3 | 41.9 | 95.3 |
| 14 | Free-type arachidonic acid | 36.9 | Calcium chloride 0.5 | 10 | 50° C. | 7 | 36.2 | 96.2 |
| 15 | Glyceride-type arachidonic acid | 78.9 | Calcium lactate 0.5 | 25 | 40° C. | 2 | 78.1 | 93.4 |

Note:
the "calcium compound (mol/mol)" is referred to as the molar ratio of the calcium compound (mol) to the polyunsaturated fatty acid material (mol); the "water (g/g)" is referred to as the weight ratio of water (g) to the calcium compound material (g).

polyunsaturated fatty acid material comprises one or more of the following substances:

a polyunsaturated fatty acid with a formula

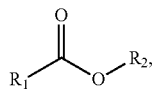

where $R_1$ is a $C_6$~$C_{40}$ alkenyl group, $R_2$ is H or a $C_1$~$C_4$ alkyl group; and a polyunsaturated fatty acid with a formula

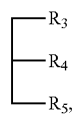

where $R_3$, $R_4$, $R_5$ are a hydroxyl or a $C_1$~$C_4$ carboxylic acid group or a $C_6$~$C_{40}$ carboxylic acid group containing one or more double bonds; $R_3$, $R_4$ and $R_5$ can be the same or different; and $R_3$, $R_4$ and $R_5$ cannot be simultaneously a hydroxyl group or a $C_1$~$C_4$ carboxylic acid group;

(iii) filtrating to obtain a solid of polyunsaturated fatty acid-calcium after completion of the reaction; and (iv) drying and crushing the solid of polyunsaturated fatty acid-calcium to obtain a free-flowing polyunsaturated fatty acid-calcium product.

2. The method according to claim 1, wherein the polyunsaturated fatty acid material is selected from the group consisting of free-type polyunsaturated fatty acid, methyl ester-type polyunsaturated fatty acid, ethyl ester-type polyunsaturated fatty acid, and glyceride-type polyunsaturated fatty acid.

3. The method according to claim 2, wherein the polyunsaturated fatty acid material is selected from the group consisting of fish oil, algae oil, linoleic acid, conjugated linoleic acid, linolenic acid, and arachidonic acid.

4. The method according to claim 1, wherein the content of the polyunsaturated fatty acid in the polyunsaturated fatty acid material is 10~100 wt %.

5. The method according to claim 1, wherein the water-soluble calcium compound material is selected from the group consisting of calcium acetate, calcium lactate, calcium chloride, calcium nitrate, calcium citrate, and calcium fumarate.

6. The method according to claim 5, wherein a molar quantity of the water-soluble calcium compound material is 0.1~0.9 relative to a molar equivalent of the polyunsaturated fatty.

7. The method according to claim 6, wherein the molar quantity of the water-soluble calcium compound material is 0.5~0.7 relative to the molar equivalent of the polyunsaturated fatty acid.

8. The method according to claim 1, wherein a water weight of dissolving the water-soluble calcium compound material is 1~40 relative to a weight equivalent of the water-soluble calcium compound material.

9. The method according to claim 1, wherein the reaction temperature is 20~100° C.

10. The method according to claim 1, wherein the reaction has a reaction time of 0.5~10 hours.

11. The method according to claim 10, wherein the reaction time is 0.5~3 hours.

* * * * *